(12) United States Patent　　(10) Patent No.:　US 11,534,132 B2
Hoppmann et al.　　(45) Date of Patent:　Dec. 27, 2022

(54) USING ULTRASOUND AND ARTIFICIAL INTELLIGENCE TO ASSESS MUSCLE STRETCH REFLEXES

(71) Applicants: University of South Carolina, Columbia, SC (US); Texas Tech University System, Lubbock, TX (US)

(72) Inventors: Richard Hoppmann, Columbia, SC (US); Jongyeol Kim, Wolfforth, TX (US)

(73) Assignees: UNIVERSITY OF SOUTH CAROLINA, Columbia, SC (US); TEXAS TECH UNIVERSITY SYSTEM, Lubbock, TX (US)

( * ) Notice: Subject to any disclaimer, the term of this patent is extended or adjusted under 35 U.S.C. 154(b) by 0 days.

(21) Appl. No.: 17/410,001

(22) Filed: Aug. 24, 2021

(65) Prior Publication Data

US 2022/0054105 A1　Feb. 24, 2022

Related U.S. Application Data

(60) Provisional application No. 63/069,217, filed on Aug. 24, 2020.

(51) Int. Cl.
*A61B 8/00*　　(2006.01)
*A61B 8/08*　　(2006.01)

(52) U.S. Cl.
CPC .............. *A61B 8/08* (2013.01); *A61B 8/486* (2013.01); *A61B 8/488* (2013.01); *A61B 8/5261* (2013.01)

(58) Field of Classification Search
CPC ........................................... A61B 8/08
See application file for complete search history.

(56) References Cited

U.S. PATENT DOCUMENTS

| 2013/0204097 A1* | 8/2013 | Rondoni | A61B 5/389 |
| | | | 600/453 |
| 2013/0231548 A1* | 9/2013 | Brown | A61B 5/004 |
| | | | 600/407 |
| 2021/0077067 A1* | 3/2021 | Labyed | A61B 8/485 |

* cited by examiner

*Primary Examiner* — Joseph M Santos Rodriguez
(74) *Attorney, Agent, or Firm* — Burr & Forman, LLP; Douglas L. Lineberry

(57) ABSTRACT

The present disclosure provides using ultrasound technology and artificial intelligence to enhance MSR assessment by making the assessment more objective, reproducible, and recordable to allow a more precise and/or personalized approach to the medical practice of individual patients via using multiple ultrasound functions and artificial intelligence to improve the accuracy and consistency of assessing reflexes and allowing MSR data to be combined with other patient medical information for improved diagnosis and management of a patient's condition.

20 Claims, 8 Drawing Sheets

USING ULTRASOUND AND ARTIFICIAL INTELLIGENCE TO ASSESS MUSCLE STRETCH REFLEXES

TECHNICAL FIELD

The present disclosure relates to employing ultrasound technology and artificial intelligence to improve MSR assessment, making same more objective, reproducible, and recordable.

BACKGROUND

Assessing muscle stretch reflexes (MSRs), more commonly known as deep tendon reflexes (DTRs), with a reflex hammer has been an important component of the comprehensive physical examination for over 150 years. There are six commonly recognized MSRs with the "knee jerk" being the most widely recognized example. The stretch reflex, or more accurately "muscle stretch reflex", is a muscle contraction in response to stretching within the muscle. The reflex functions to maintain the muscle at a constant length.

In brief, a MSR occurs when stretch receptors within a muscle are activated when the muscle is lengthened or stretched usually by the examiner tapping on the muscle tendon with a reflex hammer. This tap activates stretch receptors in the muscle spindle sending a sensory nerve impulse to a connection or synapse in the spinal cord to a motor neuron that sends an impulse back to the muscle leading to muscle contraction and the characteristic jerk of the limb being tested.

For the knee jerk, this means tapping on the patellar tendon with the reflex hammer that stretches the quadricep muscle sending a sensory signal to the spine that synapses with the motor neuron sending a motor signal back to the quadriceps muscle activating contraction and the characteristic knee jerk or brisk forward motion of the lower leg. While this process takes place, an inhibitory neural signal is sent to the opposing muscle generally on the opposite side of the joint and, in this case, the muscle opposing the quadriceps is the hamstring which is inhibited from contracting.

This local level (lower motor neuron) control of MSRs is also influenced by the neurological system higher up in the spinal cord and brain (upper motor neuron) which is typically inhibitory. If the inhibitory control is lost, the reflex can become greater than normal or hyper-reflexive. Thus, there are multiple components to MSRs including the muscle itself, peripheral nerves, the spinal cord, and the brain. In addition, the chemical and electrical activity of the muscles and nerves responsible for contraction can be affected by abnormalities in the level of electrolytes, such as calcium and magnesium, and any toxins in the body.

MSRs in the normal physiological state should be symmetrical from one side of the body to the other. In other words, the degree of knee jerk in the right knee should be approximately the same as that in the left knee. Asymmetry in response would raise the possibility of an underlying pathological process. In addition, MSR results in a patient must always be considered in the larger context of the patient's health, other physical examination findings, laboratory results, imaging results, and medical conditions.

Accurate and consistent assessment of MSRs provide important clinical information in diagnosing and managing many medical conditions. Besides the more direct neuromuscular conditions such as spinal cord injury, neurodegenerative diseases, myopathies, and strokes, MSRs are used to evaluate many everyday medical conditions such as a herniated disc in the lower back causing sciatica, assessment for neuropathy in a diabetic patient, hypothyroidism, and eclampsia in a pregnant patient.

Presently, the assessment of MSRs is highly subjective on the part of the examining practitioner, which includes many specialty and subspecialty physicians, nurses, nurse practitioners, physical assistants, and other health care providers. The examiner strikes the muscle tendon with a reflex hammer or other object and estimates the degree of response on a scale from zero to four with zero being no reflex and four being a hyperactive reflex. A reflex of 2 is considered normal. A more detailed scale of assessment is often used by adding a plus or minus to the number such as 2+ for slightly greater than normal or 2− for slightly less than normal. It is understood that reflexes can vary between individuals with a range of 1 to 3 possibly being normal for a particular individual.

An examiner's assessment of a patient's reflex is highly dependent on personal experience and skill in performing the examination. Patient characteristics can affect performing the examination such as body habitus and the patient's ability to fully participate in the examination which requires the appropriate joint position, relaxation, and following commands.

Accordingly, it is an object of the present disclosure to provide a more comprehensive as well as repeatable method of conducting MSR assessments. Herein, using ultrasound technology and artificial intelligence will make MSR assessment more objective, reproducible, and recordable.

Citation or identification of any document in this application is not an admission that such a document is available as prior art to the present disclosure.

SUMMARY

The above objectives are accomplished according to the present disclosure by providing in one embodiment, a method for improved muscle stretch reflex assessments. The method may include eliciting at least one muscle stretch reflex response in a subject, employing at least one ultrasound function to analyze the subject while the muscle stretch reflex response occurs, obtaining muscle stretch reflex data regarding the at least one muscle stretch reflex response for the subject, and analyzing the muscle stretch reflex data to determine a health condition of the subject. Further, the muscle stretch reflex data obtained from the subject may be recorded. Again, artificial intelligence may be used to analyze the muscle stretch reflex data. Still, a medical condition may be diagnosed as indicated via the muscle stretch reflex data obtained from the subject. Moreover, the muscle stretch reflex data may be combined with at least one other neuromuscular assessment data. Yet again, the at least one other neuromuscular assessment data may comprise peripheral nerve conduction velocities, electromyography, tensiomyography, or magnetic resonant imaging. Still further, the muscle stretch reflex data may be analyzed in conjunction with analyzing genetic information of the subject. Further still, the muscle stretch reflex data may be employed to manage a medical condition in the subject. Furthermore, the ultrasound function may analyze the subject prior to, during, and after elicitation of the muscle stretch reflex response. Yet further, the method may include measuring presence and magnitude of the muscle stretch reflex response.

In an alternative embodiment, a new ultrasound analysis technique is provided. The technique can include eliciting at least one muscle stretch reflex response in a subject, employing an ultrasound device in either A Mode, B Mode, M Mode or Doppler Mode to analyze the subject while the muscle stretch reflex response occurs, obtaining muscle stretch reflex data regarding the at least one muscle stretch reflex response for the subject, and analyzing the muscle stretch reflex data to determine a health condition of the subject. Further, the muscle stretch reflex data obtained from the subject may be recorded. Still, artificial intelligence may analyze the muscle stretch reflex data. Moreover, a medical condition indicated via the muscle stretch reflex data obtained from the subject may be diagnosed. Yet again, the muscle stretch reflex data may be combined with at least one other neuromuscular assessment data. Still again, the at least one other neuromuscular assessment data may include peripheral nerve conduction velocities, electro-myography, tensiomyography, or magnetic resonant imaging. Moreover, the muscle stretch reflex data may be analyzed in conjunction with genetic information of the subject. Further again, the muscle stretch reflex data may be employed to manage a medical condition in the subject. Yet again, the ultrasound device may analyze the subject prior to, during, and after elicitation of the muscle stretch reflex response. Still further, the technique may include measuring presence and magnitude of the at least one muscle stretch reflex response by analyzing muscle size changes during the at least one muscle stretch reflex response.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present disclosure will be obtained by reference to the following detailed description that sets forth illustrative embodiments, in which the principles of the disclosure may be utilized, and the accompanying drawings of which.

Figure 1:
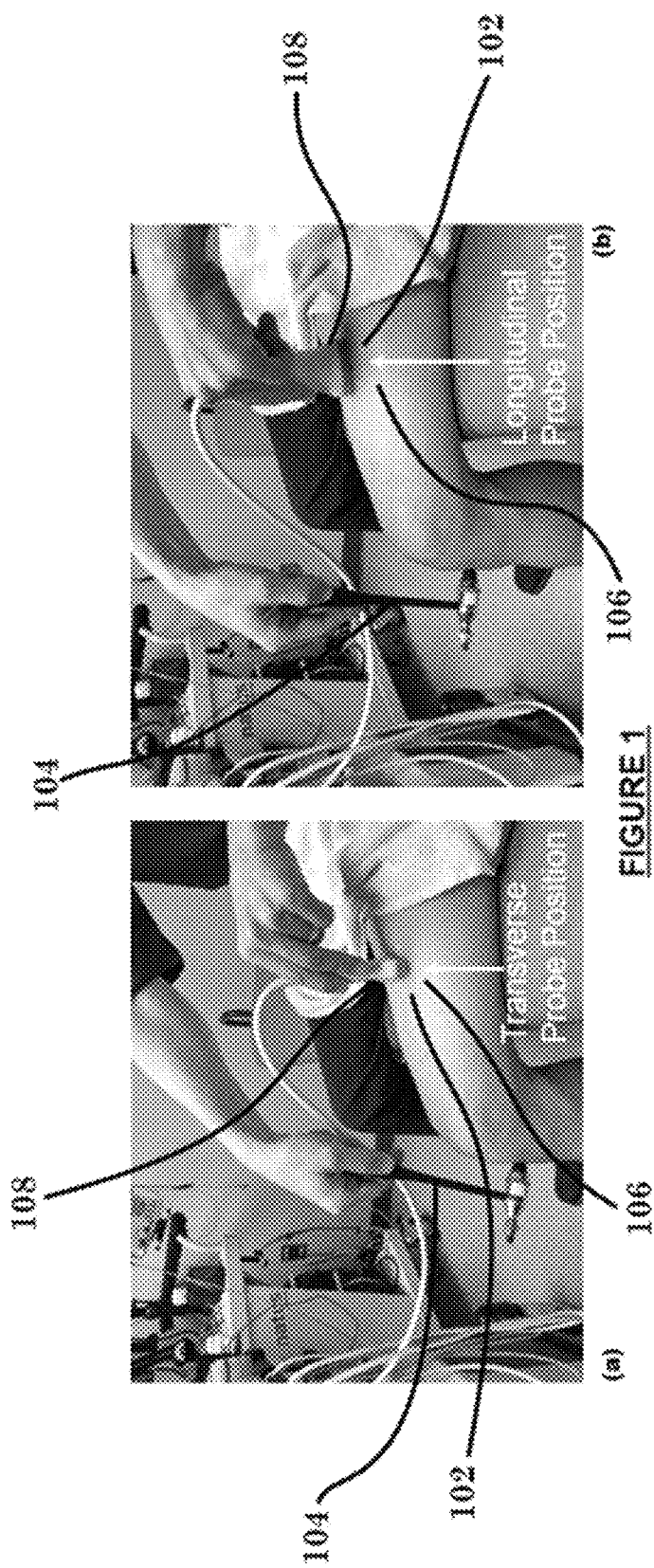
FIG. 1 shows a photograph of an ultrasound scanning probe in transverse position over the rectus femoris and vastus intermedius of the quadriceps muscle while tapping the patella tendon with a reflex hammer with the probe in transverse (a) and longitudinal (b) positions.

The figures herein are for illustrative purposes only and are not necessarily drawn to scale.

DETAILED DESCRIPTION OF A PREFERRED EMBODIMENT

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further embodiment includes from the one particular value and/or to the other particular value. The recitation of numerical ranges by endpoints includes all numbers and fractions subsumed within the respective ranges, as well as the recited endpoints. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the singular forms "a", "an", and "the" include both singular and plural referents unless the context clearly dictates otherwise.

As used herein, "about," "approximately," "substantially," and the like, when used in connection with a measurable variable such as a parameter, an amount, a temporal duration, and the like, are meant to encompass variations of and from the specified value including those within experimental error (which can be determined by e.g. given data set, art accepted standard, and/or with e.g. a given confidence interval (e.g. 90%, 95%, or more confidence interval from the mean), such as variations of +/−10% or less, +/−5% or less, +/−1% or less, and +/−0.1% or less of and from the specified value, insofar such variations are appropriate to perform in the disclosure. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

The term "optional" or "optionally" means that the subsequent described event, circumstance or substituent may or may not occur, and that the description includes instances where the event or circumstance occurs and instances where it does not.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed by the term "subject".

As used interchangeably herein, the terms "sufficient" and "effective," can refer to an amount (e.g. mass, volume, dosage, concentration, and/or time period) needed to achieve one or more desired and/or stated result(s). For example, a therapeutically effective amount refers to an amount needed to achieve one or more therapeutic effects.

As used herein, "tangible medium of expression" refers to a medium that is physically tangible or accessible and is not a mere abstract thought or an unrecorded spoken word. "Tangible medium of expression" includes, but is not limited to, words on a cellulosic or plastic material, or data stored in a suitable computer readable memory form. The data can be stored on a unit device, such as a flash memory or CD-ROM or on a server that can be accessed by a user via, e.g. a web interface.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as cancer and/or indirect radiation damage.

The effect can be therapeutic in terms of a partial or complete cure of a disease, condition, symptom or adverse effect attributed to the disease, disorder, or condition. The term "treatment" as used herein covers any treatment of cancer and/or indirect radiation damage, in a subject, particularly a human and/or companion animal, and can include any one or more of the following: (a) preventing the disease or damage from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present disclosure. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the disclosure. For example, in the appended claims, any of the claimed embodiments can be used in any combination.

All patents, patent applications, published applications, and publications, databases, websites and other published materials cited herein are hereby incorporated by reference to the same extent as though each individual publication, published patent document, or patent application was specifically and individually indicated as being incorporated by reference.

Kits

Any of the methods described herein can be presented as a combination kit. As used herein, the terms "combination kit" or "kit of parts" refers to the methods, techniques, analysis functions, AI analysis, and any additional components that are used to package, sell, market, deliver, and/or administer the methods and techniques described herein. Such additional components include, but are not limited to, packaging, ultrasound devices, muscle stretch reflex "triggering" instruments such as hammers, etc., blister packages and the like. When the methods and techniques described herein or a combination thereof and/or kit components are not administered simultaneously, the combination kit can contain each various equipment for performing the muscle stretch reflex and analysis in separate combinations and/or packages. The separate kit components can be contained in a single package or in separate packages within the kit.

In some embodiments, the combination kit also includes instructions printed on or otherwise contained in a tangible medium of expression. The instructions can provide information regarding eliciting, analyzing, recording, analyzing muscle stretch data with AI, safety information, information regarding medical analysis of various medical conditions, indications for use, and/or recommended treatment regimen(s) for the methods and techniques contained/described therein. In some embodiments, the instructions can provide directions and protocols for administering muscle stretch reflex tests and obtaining data from same from a subject. In some embodiments, the instructions can provide one or more embodiments of the methods and/or techniques such as any of the methods described in greater detail elsewhere herein.

A recorded objective measure of a particular patient's MSR would be of considerable clinical value. Multiple ultrasound functions may be used to assess MSRs. This systematic approach of using ultrasound to assess the MSR is a new and unique approach of assessment that carries tremendous diagnostic and patient management potential. Artificial intelligence will be used to improve the accuracy and consistency of assessing reflexes. Recording of the obtained ultrasound data from a muscle stretch reflex response may include capturing sound, video, images, etc., as known to those of skill in the art.

Further, the present disclosure allows MSR data to be combined with other neuromuscular assessment data such as that from peripheral nerve conduction velocities, electromyography, tensiomyography, and magnetic resonant imaging (MRI) studies, as well as other patient information such as laboratory results, other physical examination findings, concurrent medical conditions, and genetic data for improved diagnosis and management of the patient's condition, such as via treatment regimens, surgery, medication, physical therapy, etc. This combination of technology will allow a more precise or personalized approach to the medical practice of individual patients. This patent will further enhance medical understanding of MSRs and serve to advance education, research, and clinical practice related to neuromuscular diseases.

In performing the reflex examination, see FIG. 1, ultrasound device 108 may first be used to identify location 102 of the skin over the muscle tendon that will be engaged via tool 104, tool 104 may be a reflex hammer or automated adjustable ballistic device as known to those of skill in the art. Various ultrasound devices 108 can be employed for this purpose such as handheld, stationary or other styles of ultrasound devices. Examples include, but are not limited to, devices available from SONOSITE from Fujifilm, VSCAN from GE Healthcare, ACUSON P10 from Siemens Medical Solutions, VIAMO from Canon Medical Systems, CX50 from Philips, and/or POSOUND C3CV available from Hitachi. Ultrasound device 108 will then be placed on skin surface 106 over the muscle being tested (not shown) for an optimal image. A muscle stretch reflex will then be elicited in the subject, such as by striking the tendon with tool 104. Ultrasound image loops of several seconds duration can be recorded just prior to striking the muscle tendon continuing through the duration of the muscle contraction and return to the previous muscle resting state. Further, ultrasound device 108 may be placed on the subject in multiple positions, such as shown in FIG. 1 wherein ultrasound device 108 is placed in a transverse position at (a) and a longitudinal position (b) with respect to location 102.

Four different modes of ultrasound are used in medical imaging. These are: A-mode: A-mode is the simplest type of ultrasound. A single transducer scans a line through the body with the echoes plotted on screen as a function of depth. Therapeutic ultrasound aimed at a specific tumor or calculus is also A-mode, to allow for pinpoint accurate focus of the destructive wave energy.

B-mode: In B-mode ultrasound, a linear array of transducers simultaneously scans a plane through the body that can be viewed as a two-dimensional image on screen.

M-mode: M stands for motion. In m-mode a rapid sequence of B-mode scans whose images follow each other in sequence on screen enables doctors to see and measure range of motion, as the organ boundaries that produce reflections move relative to the probe.

Doppler mode: This mode makes use of the Doppler effect in measuring and visualizing blood flow. Doppler sonography plays an important role in medicine. Sonography can be enhanced with Doppler measurements, which employ the Doppler effect to assess whether structures (usually blood) are moving towards or away from the probe, and its relative velocity. By calculating the frequency shift of a particular sample volume, for example a jet of blood flow over a heart valve, its speed and direction can be determined and visualized. This is particularly useful in cardiovascular studies (sonography of the vasculature system and heart) and essential in many areas such as determining reverse blood flow in the liver vasculature in portal hypertension. The Doppler information is displayed graphically using spectral Doppler, or as an image using color Doppler (directional Doppler) or power Doppler (non directional Doppler). This Doppler shift falls in the audible range and is often presented audibly using stereo speakers: this produces a very distinctive, although synthetic, pulsing sound.

Figure 2:
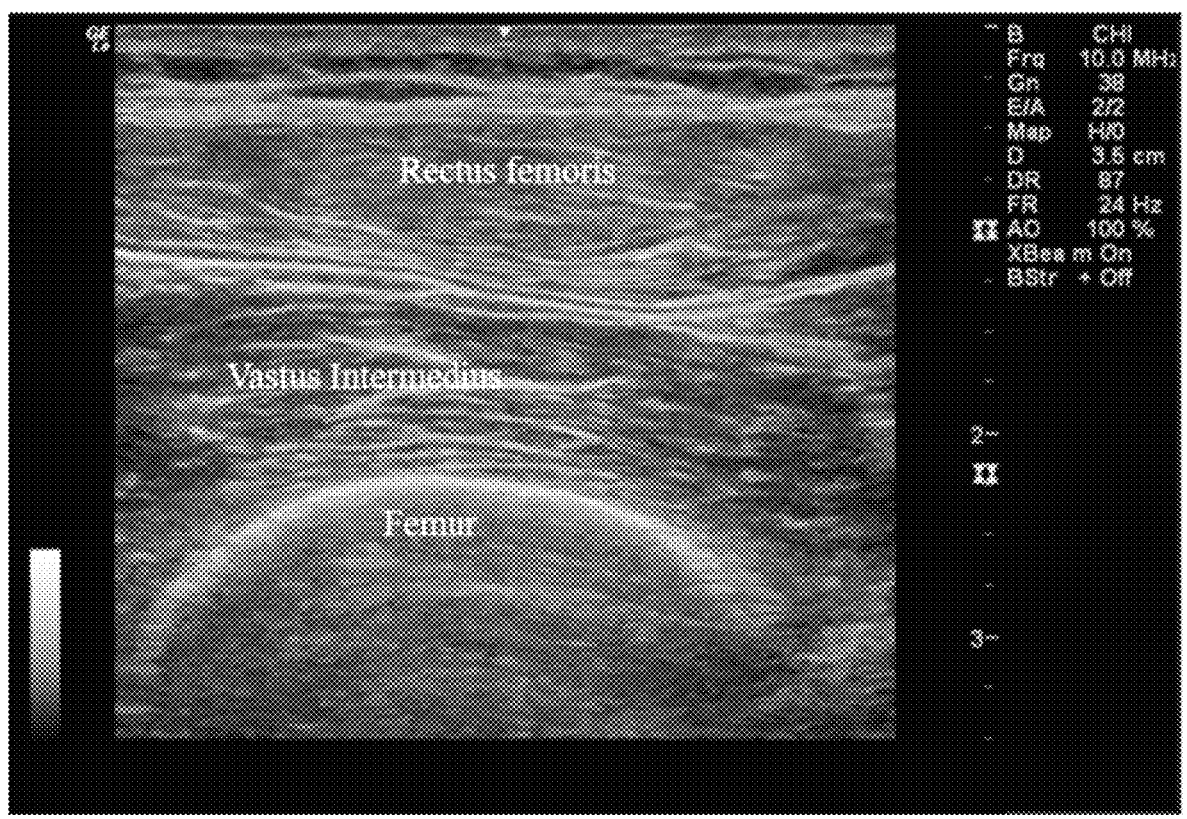
FIG. 2 transverse view of B-mode identifying rectus femoris and vastus intermedius.

For the current disclosure, recording can include B-mode (brightness mode) ultrasound scanning that will capture a real-time detailed image of the anatomical structures of the muscle and surrounding tissue, see FIG. 2.

Figure 7:
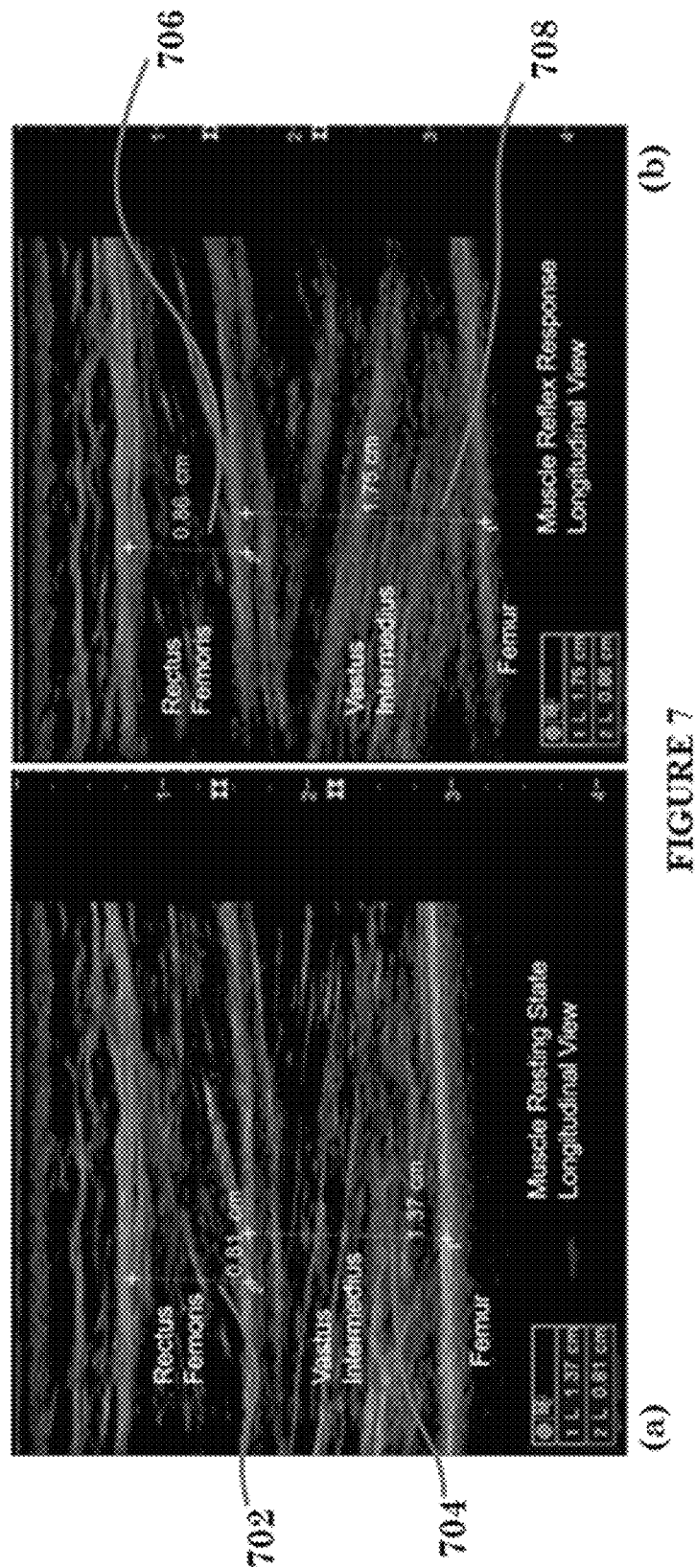
FIG. 7 shows B-mode used to measure muscle size change from resting state to contraction during reflex response.

Ultrasound machine calipers will be used to measure to one hundredth centimeter the difference in muscle dimensions before tapping the tendon and with contraction, see FIG. 7, showing measurement 702 of the rectus femoris and 704 of the vastus intermedius at muscle resting state (a) and measurement 706 of the rectus femoris and 708 of the vastus intermedius at muscle reflex response (b).

Figure 5:
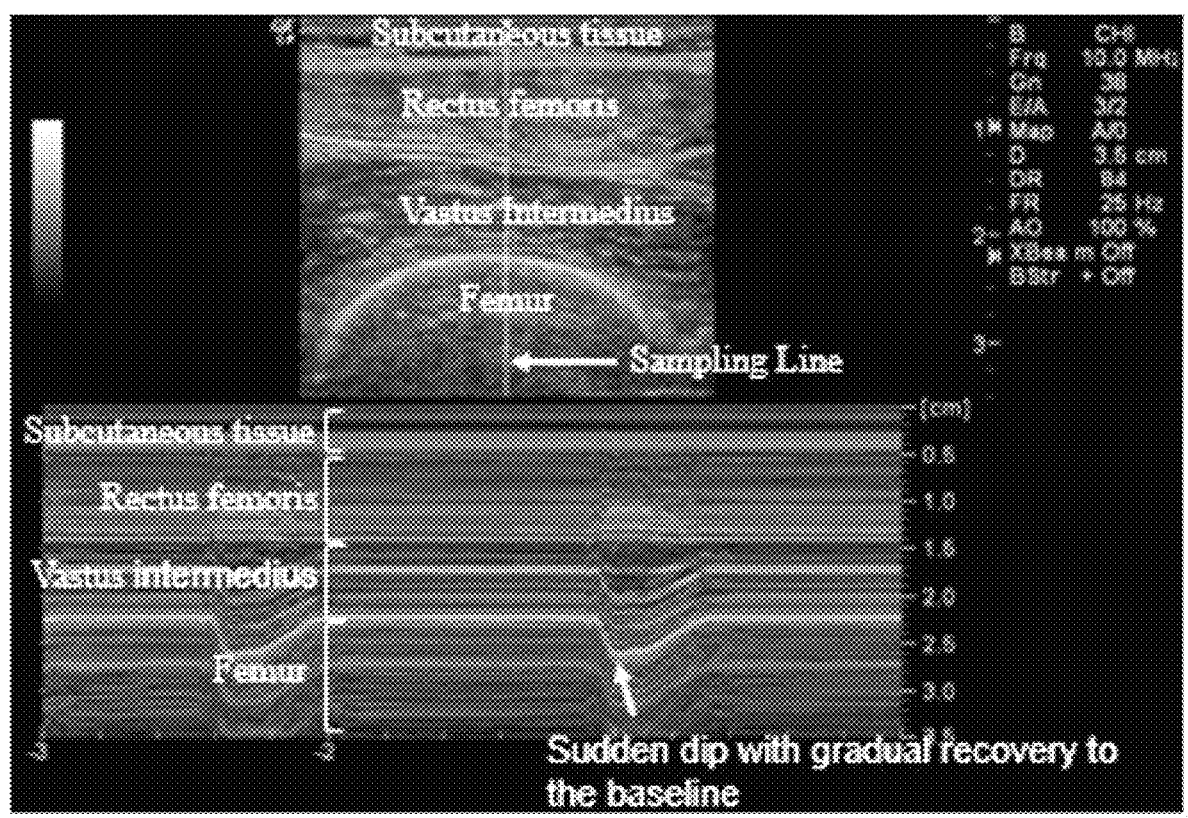
FIG. 5 shows M-mode wherein the scanline is in the middle of the vastus intermedius dipping with gradual return to the baseline due to contraction of muscle.

If available on the ultrasound device, muscle contraction can also be recorded in M-mode which records tissue movement across time, see FIG. 5. This will allow the shape and time of muscle contraction and relaxation to be precisely assessed, see FIG. 6, as well as the change in muscle dimensions with contraction, see FIG. 8. This information has not been previously assessed with ultrasound for MSRs and can provide important objective diagnostic information. Relaxation or recovery time of certain reflexes can be helpful in suggesting or establishing medical diagnoses. A common example is the slowed relaxation phase of contraction of the gastrocnemius muscle in the ankle jerk seen in hypothyroidism. However, the current disclosure is not so limited and applicable to a host of medical conditions such as, but not limited to, anxiety, Lou Gehrig's disease, multiple sclerosis, Parkinson's disease, stroke, brain injury, or spinal cord injury, etc.

There are several types of Doppler ultrasound scanning. A color Doppler helps visualize movement, speed, and direction in color. The resulting image includes a color overlay showing speed and direction. A duplex Doppler takes a standard image of a structure and graphs the data. A spectral Doppler shows a structure as graphed data. A continuous-wave Doppler sends a continuous stream of soundwaves, which allows the ultrasound to more accurately measure structures moving at faster speeds. Power Doppler is a form of color Doppler that is more sensitive to flow or movement than color Doppler but does not give direction of flow.

For the current disclosure, measurements in the various ultrasound Doppler modes, which detect direction of motion and/or velocity of motion to varying degrees, can also be performed. These include color Doppler, spectral Doppler, and power Doppler. Although Doppler is used primarily to measure blood flow it can provide information on body tissue movement as well and indicate if the MSR is intact, see FIGS. 3 and 4.

Another order of magnitude of improved reproducibility and standardization of MSR assessment can be achieved by using an automated device capable of delivering a calibrated, focused tap or vibratory blow to the muscle tendon while assessing the MSR with herein described ultrasound applications.

Digital data from the various ultrasound assessment methods of MSR described herein can be combined and analyzed with artificial intelligence developed using supervised and/or unsupervised training methods in patients with disease and adequate controls to significantly expand the level of assessment and understanding of an individual patient's condition. AI in healthcare and medicine means using data more effectively through machine learning algorithms to produce positive patient outcomes.

The sheer amount of data created through IoT-enabled devices, the electronic medical record (EMR), and ever-expanding quantities of genetic data has made possible a large number of applications of artificial intelligence in healthcare. The underlying value of artificial intelligence is to enhance human decision-making and automate processes that are time- or resource-intensive for humans to perform. This promise relies on data—capturing it, analyzing, and using it to provide precise, data-driven answers to critical questions.

Prediction forms a core component of what healthcare professionals do every day. AI can operate as a fast, accurate, and in the long run, cost-effective method to assist human experience and intuition through predictive analytics. AI is not meant to replace doctors, but rather empower healthcare professionals by adding a data-driven context that delivers the right information at the right time, allowing them to make more informed decisions.

Healthcare applications that leverage artificial intelligence can be used to make more accurate diagnoses, identify at-risk populations, manage and assign administrative resources, forecast the potential value of research projects, and better understand how patients will respond to medicines and treatment protocols.

In addition, ultrasound assessment data can be combined with other neuromuscular assessment data such as peripheral nerve conduction velocities and electromyography results as well as other patient information such as pertinent laboratory results, physical examination measurements, genetic data, and magnetic resident imaging (MRI) and analyzed with artificial intelligence algorithms and deep learning to not only improve individual patient care but also advance our understanding of neuromuscular diseases and other conditions affecting the MSRs.

Novel elements of this disclosure include:

1. Determining objective measurements of muscle stretch reflexes.
2. The use of ultrasound to assess muscle stretch reflexes.
3. The use of ultrasound B-mode to assess muscle stretch reflexes.
4. The use of ultrasound M-mode to assess muscle stretch reflexes.
5. The use of ultrasound Doppler (color, spectral, and power) to assess muscle stretch reflexes.
6. The use of artificial intelligence to assess muscle stretch reflexes.
7. Combining muscle stretch reflex data with other patient data with artificial intelligence to enhance patient diagnoses and management.
8. Combining an automated adjustable ballistic tendon device with ultrasound assessment of muscle stretch reflexes.

Ultrasound can be used to assist with the physical examination of muscle stretch reflexes or deep tendon reflexes such as the knee jerk. Objective data can be obtained that add value to the examination and assist with diagnosis and management of patients with neuromuscular diseases and other conditions that affect the neuromuscular system.

At present, the examiner's estimate of muscle stretch reflexes on physical examination is highly subjective. This subjective approach severely limits the value of MSRs in diagnosing and managing patients with possible neuromuscular diseases or neuromuscular effects from other diseases or trauma.

This disclosure will dramatically improve on the subjective nature of reflex data. It will provide visual, measurable, and repeatable data for analysis that can be saved for future reference on the patient. The objective data will also be amenable to artificial intelligence analysis independently and in combination with other patient data. Having objective repeatable reflex data will dramatically advance the value of the reflex assessment and fundamentally change the clinical approach to the patient neuromuscular examination.

The applications for this approach to reflex assessment would be quite large. Tendon reflex examination is standard for a comprehensive physical examination, standard for a neurological examination, and used for many common diseases and medical conditions that can affect the neuromuscular system and the muscle stretch reflex. These would include nearly all neurological and muscular conditions and many conditions that can affect the MSR such as diabetes, hypothyroidism, eclampsia, herniated disc disease, etc. Thus, there will be many clinicians, including almost all physicians as well as nurses and physician assistants, who would be interested in this ultrasound/AI reflex examination approach. There is an ever-expanding number of ultrasound manufacturers that would be interested in such an ultrasound application for their ultrasound systems.

There will be a number of competitive advantages for those companies licensing this disclosure and virtually all ultrasound manufacturers will likely be interested. Advantages include ultrasound systems having a new application that provides a marked improvement in patient assessment of a commonly performed component of the physical examination. This can provide an objective, recordable assessment of muscle contraction that will enhance patient diagnosis as well as management and ongoing assessment of the patient. This will also be a valuable clinical and basic science research tool for studying neuro-muscular and other diseases. For those teaching neuro-muscular physiology, pathophysiology, and the physical examination this disclosure will likewise be of great value by providing valuable educational materials and hands-on laboratory teaching opportunities of the physical examination and neuromuscular diseases for a broad array of learners.

This disclosure could also lead to further development of neuromuscular assessment laboratories that could provide greater services and generate additional revenue for performing a more comprehensive assessment of all MSRs.

FIG. 1 shows at (a) an ultrasound scanning probe in the transverse position (across the short axis of the muscle length) over the rectus femoris and vastus intermedius muscles of the quadriceps muscle while tapping the patellar tendon with a reflex hammer. At (b), the scanning probe is in the longitudinal position (along the long axis of the muscle length).

FIG. 2 show a transverse view of B-mode (brightness mode) ultrasound image identifying the rectus femoris and vastus intermedius muscles and the femur bone of the upper leg beneath the ultrasound probe.

Figure 3:
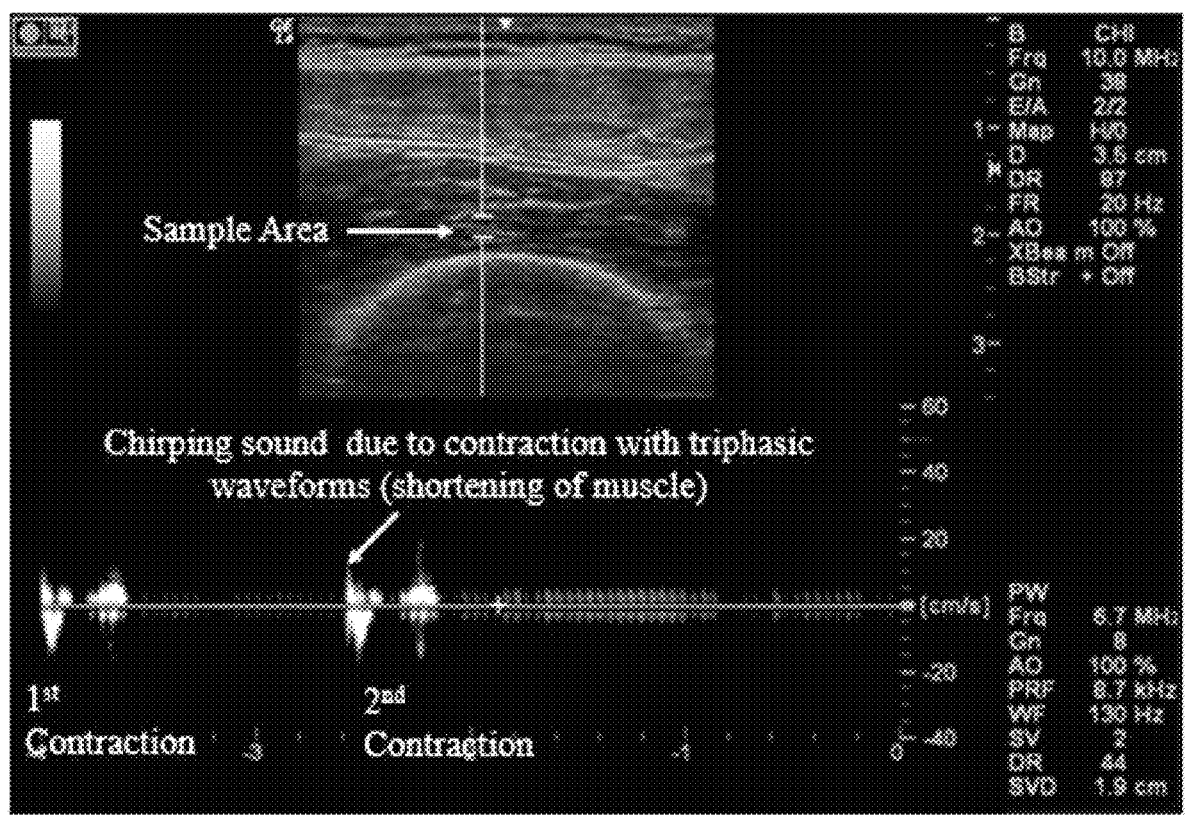
FIG. 3 spectral Doppler-mode scanning the vastus intermedius, a chirping sound with biphasic or triphasic waveform.

FIG. 3 is a transverse view of spectral Doppler-mode image with the sample area in the vastus intermedius as the patellar tendon is struck with a reflex hammer resulting in a chirping sound indicating the MSR is intact. The sound coincides with the biphasic or triphasic waveform due to the velocity and direction of muscle contraction and relaxation. The tendon was struck twice giving two sets of contractions and spectral Doppler waves.

Figure 4:
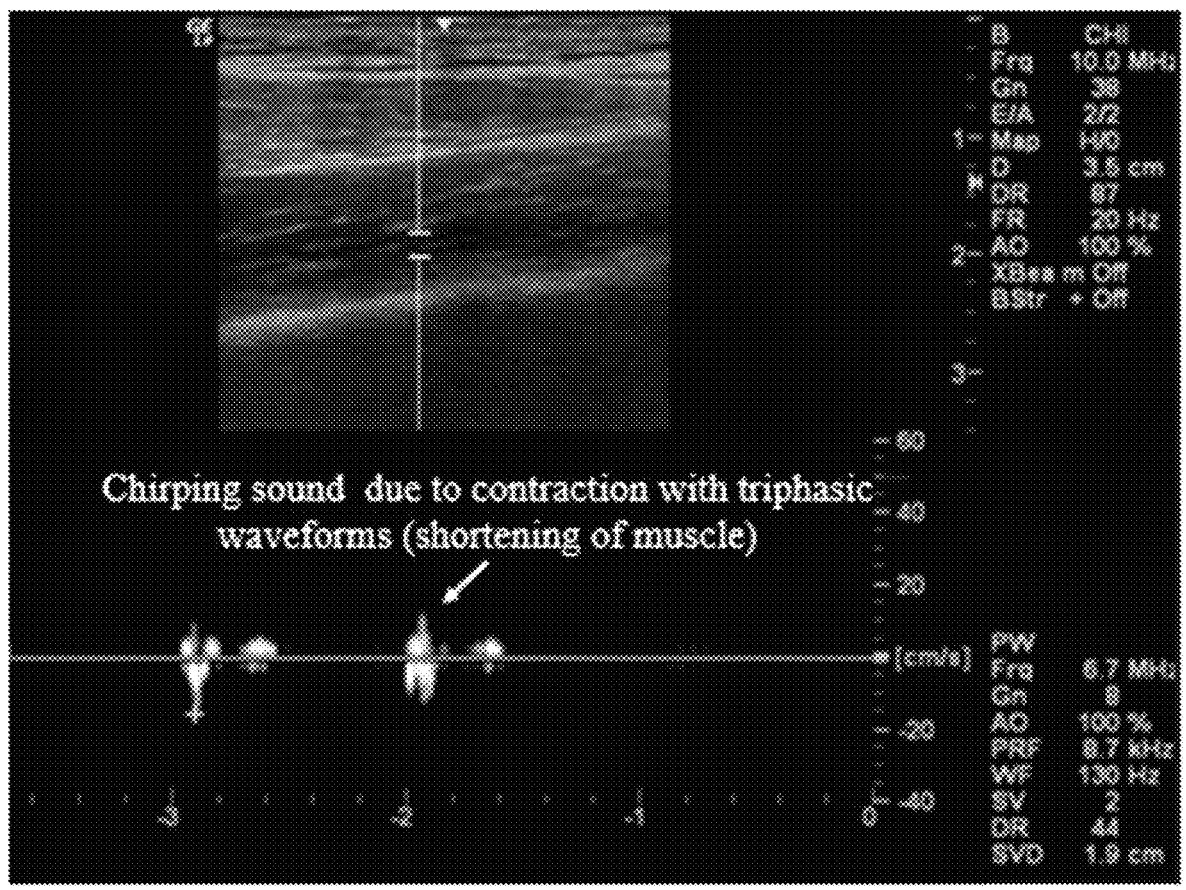
FIG. 4 shows Doppler-mode—putting the scan line in the middle of vastus intermedius, dipping with gradual return to the baseline due to contraction of muscle.

FIG. 4 is the same as FIG. 3 except with the probe in the longitudinal orientation.

FIG. 5 is a transverse view using M-mode (motion mode) ultrasound wherein the sampling line is in the middle of the rectus femoris and vastus intermedius muscles. On the top half of the figure is a B-mode image with the sampling line which represents a narrow ultrasound slice of the tissue that is shown in the bottom half of the figure across time. In practice this is viewed as a video sample of the slice across time. The various levels of tissue in the thin slice from the subcutaneous tissue just under the ultrasound probe down to the femur are identified in the figure. With striking of the patellar tendon with a reflex hammer the muscle will contract and then relax. The motion of muscle contraction and relaxation are detected across time and visualized in the lower half of the figure. The sudden clip indicated muscle contraction with striking of the muscle tendon. The patella tendon was struck twice during this time period.

Figure 6:
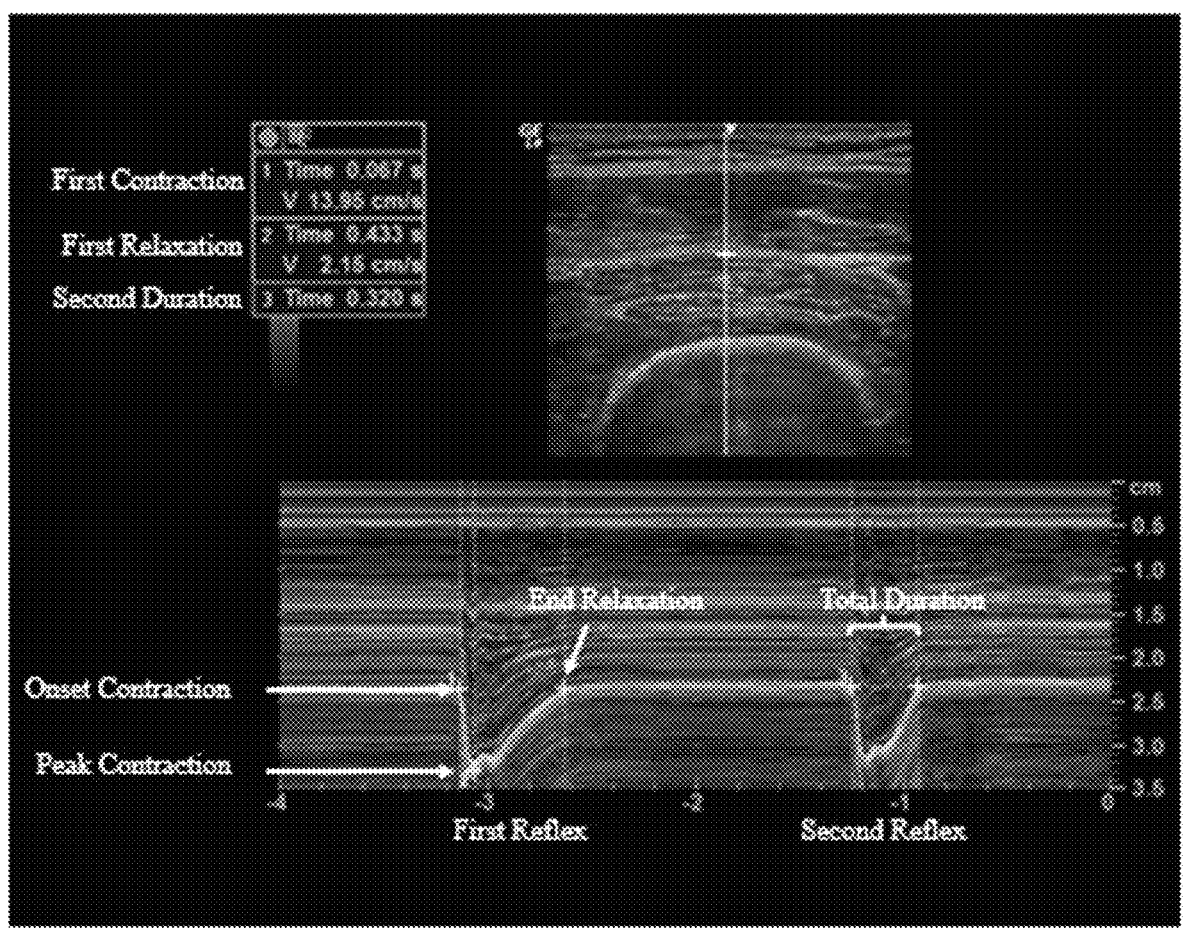
FIG. 6 shows M-mode calculating the speed of contraction of muscles.

FIG. 6 shows M-mode calculation of the speed of contraction, relaxation, and total duration of the reflex which are calculated by the ultrasound system after a video segment is saved and calipers are used to identify the points of interest. Distance and velocity results are displayed in the measurement box in the upper left position of the figure. For the first reflex, the time for full contraction was 0.067 sec with a velocity of 13.95 cm/sec. Relaxation of the first reflex took 0.433 sec at a velocity of 2.15 cm/sec. The total time for the second reflex from the initial contraction through full relaxation back to resting state was 0.320 seconds.

FIG. 7 shows B-mode and caliper markings used to measure change in muscle size of the rectus femoris and vastus intermedius muscles in a longitudinal view from resting state at (a) to contraction (thickening) at (b) during a reflex response. Rectus femoris increased from 0.81 cm at rest to 0.86 cm with contraction. Vastus intermedius increased from 1.37 cm at rest to 1.75 cm with contraction.

Figure 8:
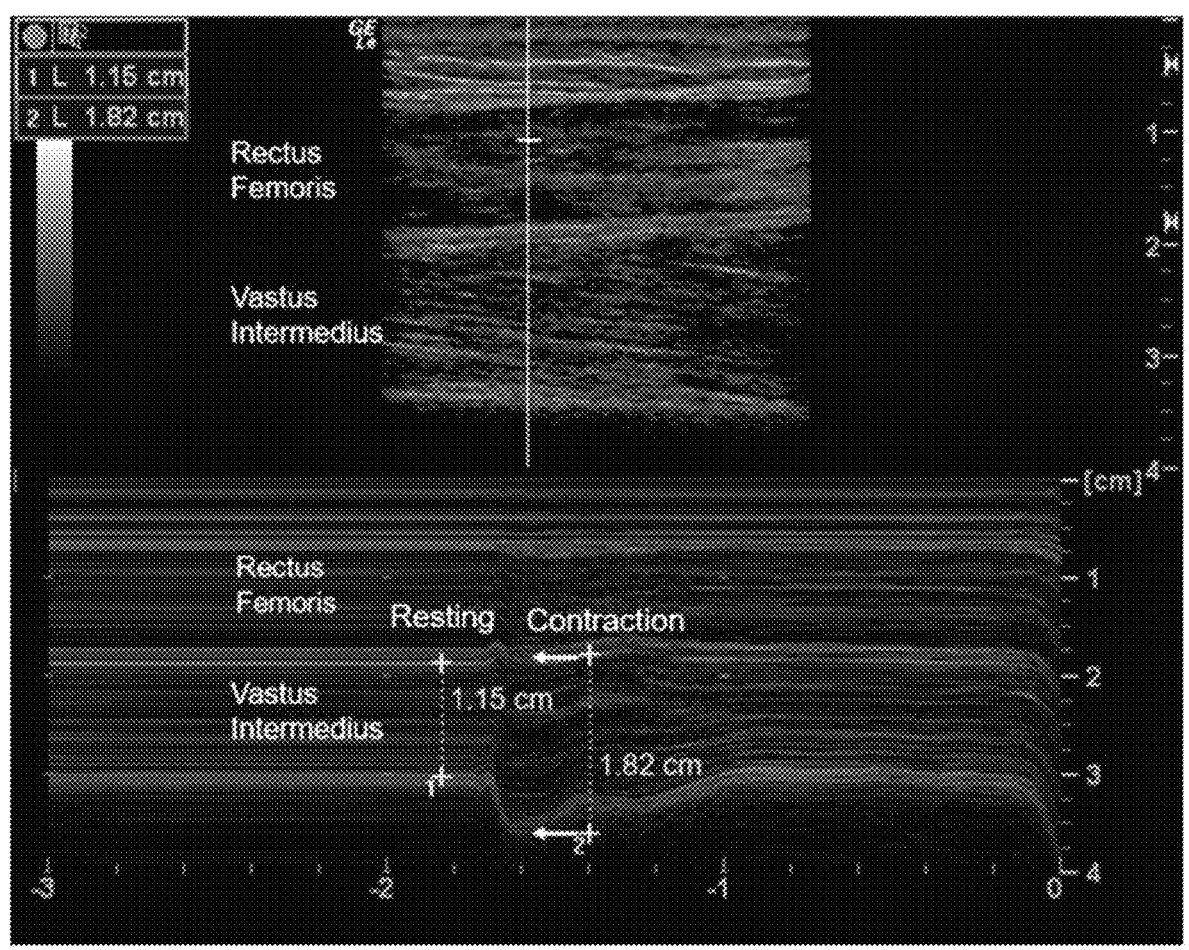
FIG. 8 shows M-mode assessment of vastus intermedius in resting state and then contraction during reflex response in the longitudinal view.

FIG. 8 shows M-mode assessment measurement of the vastus intermedius muscle in a longitudinal view from the resting state (1.15 cm) to contraction (1.82 cm maximum thickness between the white arrows) during a reflex response.

Various modifications and variations of the described methods, pharmaceutical compositions, and kits of the disclosure will be apparent to those skilled in the art without departing from the scope and spirit of the disclosure. Although the disclosure has been described in connection with specific embodiments, it will be understood that it is capable of further modifications and that the disclosure as claimed should not be unduly limited to such specific embodiments. Indeed, various modifications of the described modes for carrying out the disclosure that are obvious to those skilled in the art are intended to be within the scope of the disclosure. This application is intended to cover any variations, uses, or adaptations of the disclosure following, in general, the principles of the disclosure and including such departures from the present disclosure come within known customary practice within the art to which the disclosure pertains and may be applied to the essential features herein before set forth.

What is claimed is:

1. A method for improved muscle stretch reflex assessments comprising:
   eliciting at least one muscle stretch reflex response in a subject to analyze neurological and muscular components of the at least one muscle stretch reflex response;
   employing at least one ultrasound device to analyze the subject while the muscle stretch reflex response occurs via measuring at least one muscle dimension with ultrasound machine calipers;
   obtaining muscle stretch reflex data regarding the at least one muscle stretch reflex response for the subject wherein the muscle stretch reflex data includes measuring the at least one muscle dimension with ultrasound machine calipers before eliciting at least one muscle stretch reflex response and measuring at least one muscle dimension with ultrasound machine calipers when muscle contraction occurs due to eliciting the at least one muscle stretch reflex;
   analyzing the muscle stretch reflex data to determine a health condition of the subject by;
      comparing the at least one muscle dimension obtained prior to the at least one muscle stretch reflex response with the at least one muscle dimension obtained during the at least one muscle stretch reflex; and
      analyzing:
         activation of at least one stretch receptor in at least one muscle spindle,
         at least one sensory nerve impulse from the at least one stretch receptor to at least one spinal cord synapse with at least one motor neuron; and
         at least one motor nerve impulse from the at least one spinal cord synapse.

2. The method of claim 1, further comprising recording the muscle stretch reflex data obtained from the subject.

3. The method of claim 1, wherein a computer or processor uses at least one artificial intelligence algorithm to analyze the muscle stretch reflex data.

4. The method of claim 1, further comprising diagnosing a medical condition indicated via the muscle stretch reflex data obtained from the subject.

5. The method of claim 1, further comprising combining the muscle stretch reflex data with at least one other neuromuscular assessment data obtained from at least one physical examination.

6. The method of claim 5, wherein the at least one other neuromuscular assessment data comprises peripheral nerve conduction velocities, electromyography, tensiomyography, or magnetic resonant imaging.

7. The method of claim 1, further comprising analyzing the muscle stretch reflex data in conjunction with separately obtained laboratory genetic information of the subject.

8. The method of claim 1, further comprising employing the muscle stretch reflex data to manage a medical condition in the subject.

9. The method of claim 1, wherein the ultrasound function analyzes the subject prior to, during, and after elicitation of the muscle stretch reflex response.

10. The method of claim 1, further comprising measuring presence and magnitude of the muscle stretch reflex response.

11. A new ultrasound analysis technique comprising:
   eliciting at least one muscle stretch reflex response in a subject;
   employing an ultrasound device in either A Mode, B Mode, M Mode or Doppler Mode to analyze the subject while the muscle stretch reflex response occurs;
   obtaining muscle stretch reflex data regarding the at least one muscle stretch reflex response for the subject;
   obtaining muscle stretch reflex data regarding the at least one muscle stretch reflex response for the subject wherein the muscle stretch reflex data includes measuring the at least one muscle dimension with ultrasound machine calipers before eliciting at least one muscle stretch reflex response and measuring at least one muscle dimension with ultrasound machine calipers when muscle contraction occurs due to eliciting the at least one muscle stretch reflex; and
   analyzing the muscle stretch reflex data to determine a health condition of the subject by;
      comparing the at least one muscle dimension obtained prior to the at least one muscle stretch reflex response with the at least one muscle dimension obtained during the at least one muscle stretch reflex; and
      analyzing:
         activation of at least one stretch receptor in at least one muscle spindle,
         at least one sensory nerve impulse from the at least one stretch receptor to at least one spinal cord synapse with at least one motor neuron; and
         at least one motor nerve impulse from the at least one spinal cord synapse.

12. The technique of claim 11, further comprising recording the muscle stretch reflex data obtained from the subject.

13. The technique of claim 11, wherein a computer or processor uses at least one artificial intelligence algorithm to analyze the muscle stretch reflex data.

14. The technique of claim 11, further comprising diagnosing a medical condition indicated via the muscle stretch reflex data obtained from the subject.

15. The technique of claim 11, further comprising combining the muscle stretch reflex data with at least one other neuromuscular assessment data obtained from at least one physical examination.

16. The technique of claim 15, wherein the at least one other neuromuscular assessment data comprises peripheral nerve conduction velocities, electromyography, tensiomyography, or magnetic resonant imaging.

17. The technique of claim 11, further comprising analyzing the muscle stretch reflex data in conjunction with separately obtained laboratory genetic information of the subject.

18. The technique of claim 11, further comprising employing the muscle stretch reflex data to manage a medical condition in the subject.

19. The technique of claim 11, wherein the ultrasound device analyzes the subject prior to, during, and after elicitation of the muscle stretch reflex response.

20. The technique of claim 11, further comprising measuring presence and magnitude of the at least one muscle stretch reflex response by analyzing muscle size changes during the at least one muscle stretch reflex response.

* * * * *